(12) United States Patent
Le Comte et al.

(10) Patent No.: US 6,818,182 B2
(45) Date of Patent: Nov. 16, 2004

(54) DEVICE FOR PROCESSING SAMPLES OF BLOOD PRODUCTS

(75) Inventors: Roger Le Comte, Perols (FR); Serge Champseix, Tarnac (FR); Henri Champseix, Montferrier sur Lez (FR)

(73) Assignee: ABX Parc Euromedecine, Montpellier (FR)

(*) Notice: Subject to any disclaimer, the term of this patent is extended or adjusted under 35 U.S.C. 154(b) by 378 days.

(21) Appl. No.: 09/909,996

(22) Filed: Jul. 23, 2001

(65) Prior Publication Data

US 2002/0021983 A1 Feb. 21, 2002

(30) Foreign Application Priority Data

Jul. 21, 2000 (FR) .............................................. 00 09623

(51) Int. Cl.⁷ ........................ G01N 21/00; G01N 33/00; G01N 31/00; B01L 3/02
(52) U.S. Cl. ........................ 422/65; 422/100; 422/63; 422/67; 422/68.1
(58) Field of Search ............................ 422/100, 63–67, 422/68.1; 436/180; 73/863.32, 863.91, 864, 864.31, 864.01, 864.24, 864.25, 864.74

(56) References Cited

U.S. PATENT DOCUMENTS

| | | | | |
|---|---|---|---|---|
| 3,644,095 A | * | 2/1972 | Netheler et al. ............... | 422/65 |
| 4,039,286 A | * | 8/1977 | Keller et al. ................... | 436/47 |
| 4,609,017 A | * | 9/1986 | Coulter et al. ................. | 141/1 |
| 4,861,553 A | * | 8/1989 | Mawhirt et al. ............... | 422/65 |
| 4,921,676 A | | 5/1990 | Otani | |
| 5,380,666 A | * | 1/1995 | Wuerschum ................. | 436/54 |
| 5,482,863 A | * | 1/1996 | Knobel .......................... | 436/54 |
| 5,665,309 A | | 9/1997 | Champseix et al. | |
| 5,948,360 A | * | 9/1999 | Rao et al. ...................... | 422/65 |
| 5,959,221 A | * | 9/1999 | Boyd et al. .............. | 73/864.24 |
| 6,045,755 A | * | 4/2000 | Lebl et al. ..................... | 422/65 |
| 6,056,921 A | * | 5/2000 | Rao et al. ...................... | 422/65 |
| 6,066,300 A | * | 5/2000 | Carey et al. ................. | 422/104 |
| 6,337,053 B1 | * | 1/2002 | Tajima ........................ | 422/102 |
| 6,413,780 B1 | * | 7/2002 | Bach et al. ................... | 436/48 |
| 6,482,363 B1 | * | 11/2002 | Dobelin ....................... | 422/100 |
| 6,498,037 B1 | * | 12/2002 | Carey et al. .................. | 436/50 |
| 2002/0110493 A1 | * | 8/2002 | Dales et al. ................. | 422/100 |
| 2002/0127727 A1 | * | 9/2002 | Bach et al. .................... | 436/48 |

FOREIGN PATENT DOCUMENTS

| | | |
|---|---|---|
| DE | 19504748 | 4/1996 |
| EP | 0275119 | 7/1988 |
| JP | 57063122 | 4/1982 |

* cited by examiner

Primary Examiner—Jill Warden
Assistant Examiner—Brian R Gordon
(74) Attorney, Agent, or Firm—Dennison, Schultz, Dougherty & MacDonald

(57) ABSTRACT

A device for processing samples of blood products contained in tubes (18) closed by bungs (20) and loaded into cassettes (12), includes transfer component (10) designed to individually move the cassettes (12) on a pre-determined path, agitation component (30) having at least one pick-up mechanism (32) capable of being actuated by driving component (88) to pick up at least one selected tube (18) from a cassette (12) immobilised on the path, to move said tube away from the cassette, to agitate the tube and replace it in the cassette, and sampling component (34) designed to draw off a given sample quantity from the pre-agitated tube which has been replaced in the cassette.

14 Claims, 10 Drawing Sheets

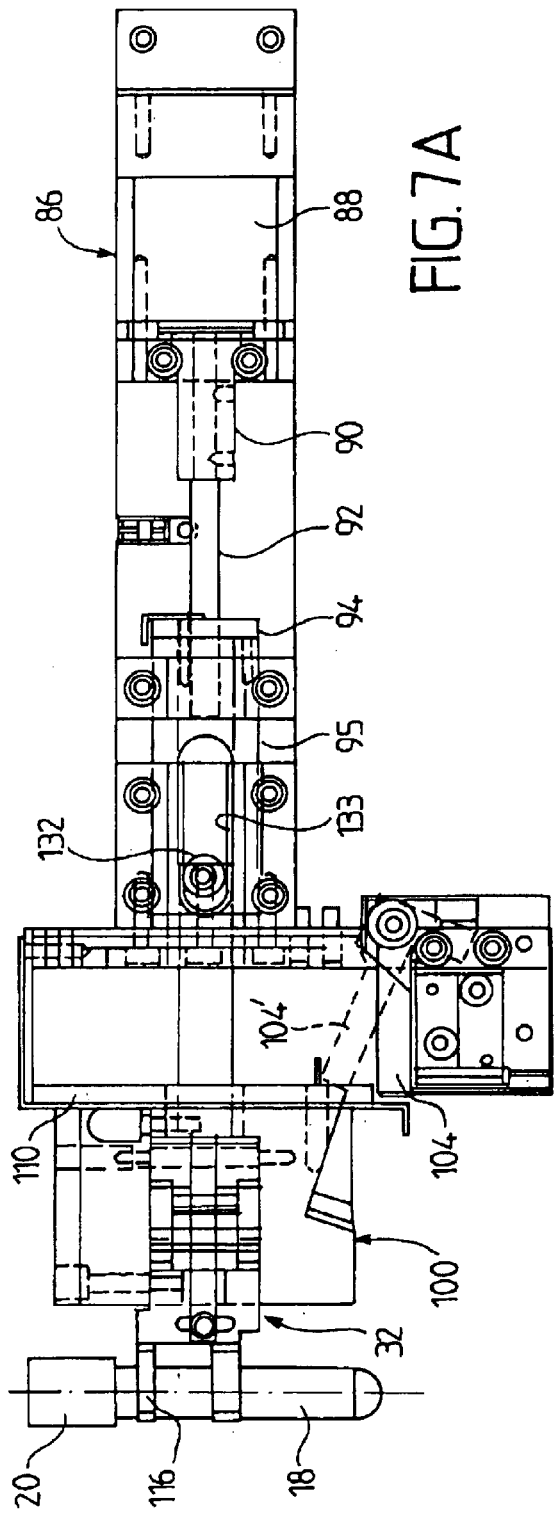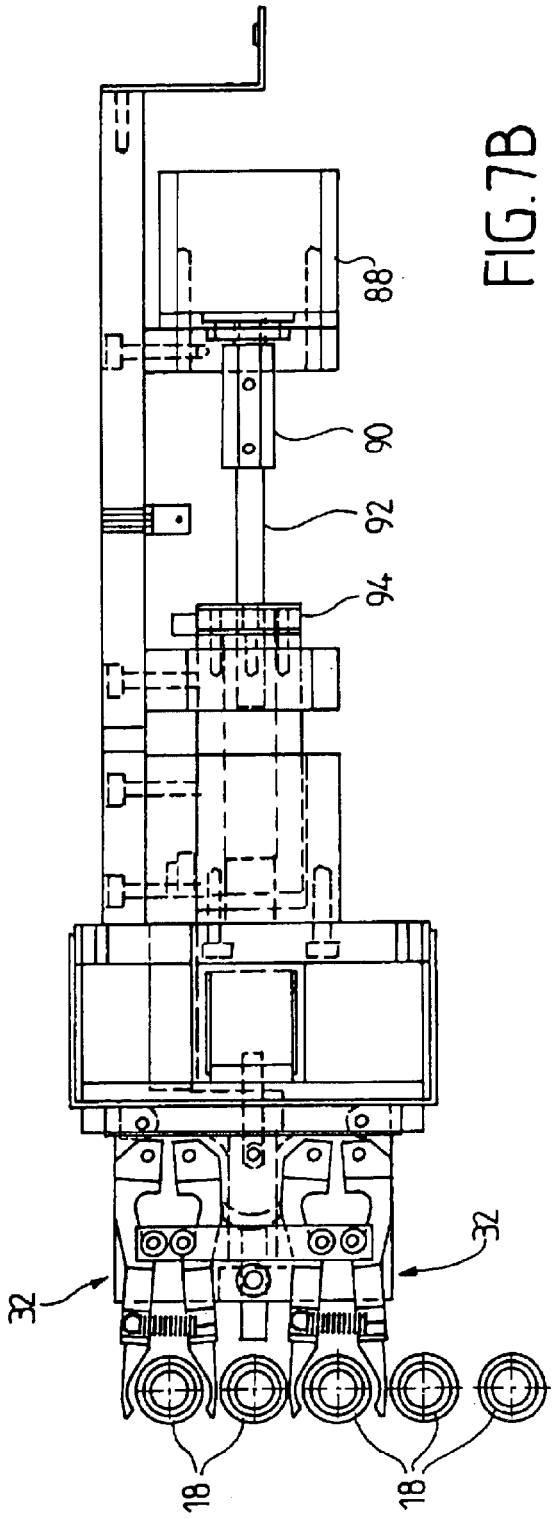

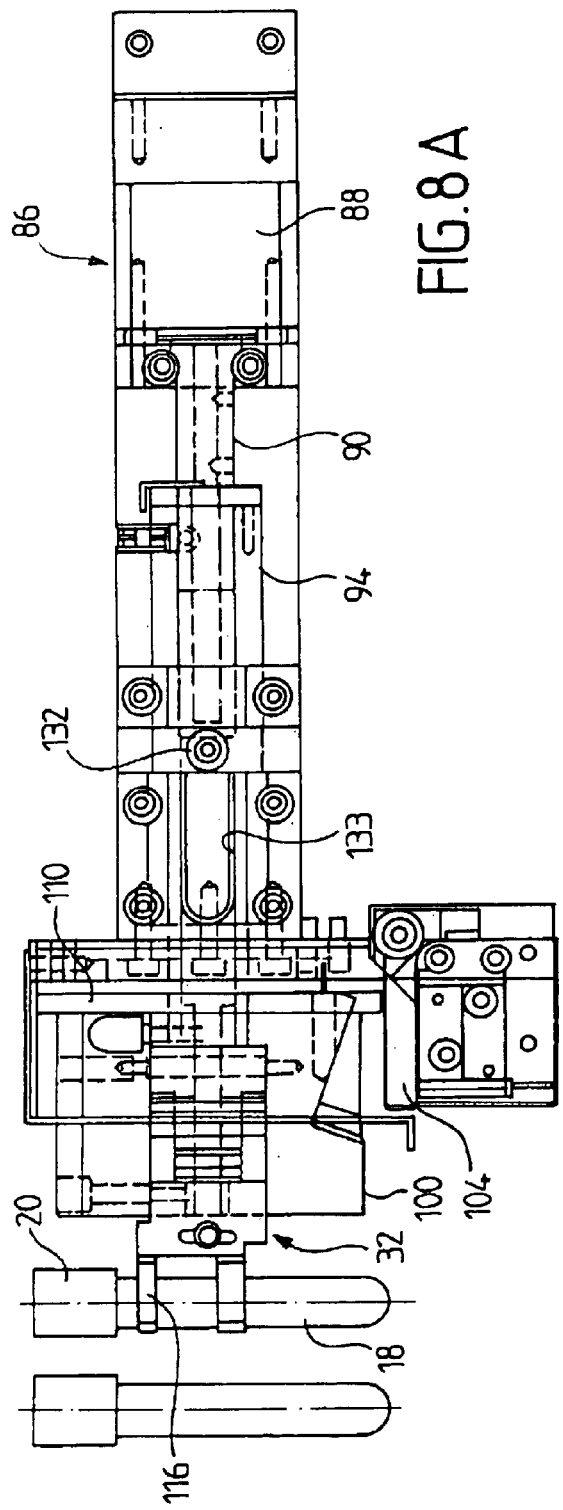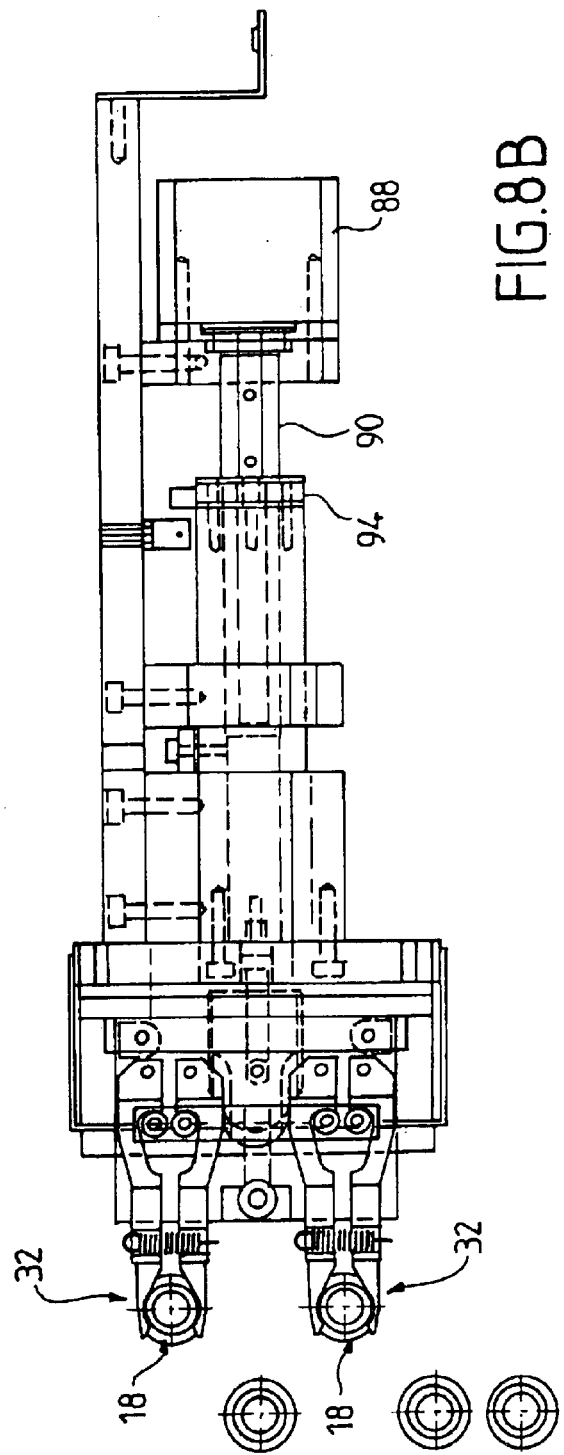

DEVICE FOR PROCESSING SAMPLES OF BLOOD PRODUCTS

The invention relates to haematological analysers designed to automatically analyse samples of blood products.

FIELD OF THE INVENTION

It relates particularly to a device for processing samples of blood products contained in tubes closed by means of bungs and loaded into cassettes, and incorporating means of agitation capable of agitating the tubes, together with means of sampling capable of collecting at least one sample from a pre-agitated tube.

Such devices are designed to agitate the tube in order to mix the constituents of the blood product which it contains, and to then take a sample having a composition that is both homogeneous and representative of the blood product to be analysed.

BACKGROUND FOR THE INVENTION

In particular an automatic device is known, according to U.S. Pat. No. 3,231,244 for the mixing of blood products which includes a rotary drum incorporating slots designed to hold tubes containing such products. The tubes are arranged radially relative to the axis of rotation of the drum, so that their respective bungs are directed outward. In fact, this is only an agitation device which has the drawback that the tubes have to be loaded manually onto the drum, then removed manually from the drum once the agitation process has been completed.

Also, a device is known according to EP-A-0 061 317 for the agitation and sampling of specimens of blood products, wherein the tubes containing the products are grouped in cassettes which are placed manually in a rotary drum. The purpose of the latter is to mix the blood products by rotation and to immobilise a cassette in an essentially vertical position so that tubes it contains are held with their bungs facing downward. A sampling station is provided to draw a sample from a tube in a cassette after piercing the tube bung. After analysis, the cassettes are manually removed from the drum.

The principal drawback of this known device is that it is incapable of rotating the drum, thereby agitating the set of tubes, during the sampling operation itself.

A device is also known, according to FR-A-2 730 315, for the agitation and sampling of specimens of blood products from tubes grouped in cassettes. This known device includes a cassette holder designed to support and agitate at least one cassette loaded with at least one tube, together with at least one sampling station designed to pierce the tube bung and draw off the specimen. By virtue of the fact that the sample is taken from a tube, away from the cassette, there is no necessity to provide means of locking the holder to prevent rotation during the sampling operation.

This known device is mechanically very complex, reflected in its unduly high cost.

A further device is known, according to FR-A-2 692 358, for the transfer, agitation and sampling of blood product specimens which includes a mobile carriage designed to remove a cassette loaded with specimen tubes from a storage receptacle and to transfer the cassette to a rotary carriage. The latter agitates the specimens and can be immobilised to allow samples to be collected from the cassette tubes by means of a sampling station.

This devices presents essentially the same shortcomings as those cited previously.

The aim of the invention disclosed is notably to overcome the aforementioned shortcomings.

BRIEF SUMMARY OF THE INVENTION

In particular, the invention proposes a device for processing samples of blood products contained in tubes loaded into cassettes, whereby agitation of the tubes is performed independently of the cassettes, which avoids having to agitate the cassettes themselves.

The invention also aims to provide such a processing device which facilitates agitation of a tube independently of the cassette, and then enables a specimen of blood products to be collected from the tube after it has been replaced in the cassette.

The invention also aims to provide a device as described above, wherein the cassettes present a range of different loading or unloading options for the tubes.

The invention also aims to provide such a device that can be readily integrated into a line of several blood analysis units.

To this end, the invention proposes a processing device of the type defined in the introduction, which includes means of transfer designed to move the cassettes individually on a pre-determined path, and in which the means of agitation incorporate at least one pick-up mechanism designed to pick up at least one selected tube from a cassette immobilised on the path, to remove said tube from the cassette, to agitate the tube and to replace it in the cassette, and in which the sampling means include at least one needle designed to draw a given sample quantity from the tube that has been pre-agitated and replaced in the cassette.

Thus, the device according to the invention agitates the tubes after they have been removed from the cassette, and draws samples from the tubes which, following agitation, have been replaced in the cassette.

Consequently, this avoids the necessity of agitating the entire cassette as in the majority of the devices according to the previous state of the art.

This has the further advantage that the cassettes can be moved along a chosen path, in particular a linear path, thereby facilitating integration of the invention into a line of haematological analysis units.

In addition, by virtue of the fact that loading and unloading of the tubes is performed by means of a cassette, which is moved by transfer means, these operations can be carried out in different ways, in particular via the top and via the side of the cassette.

Furthermore, by virtue of the fact that the means of agitation are applied to one or more tubes, and not to a cassette, the overall dimensions of the device are reduced, which contributes to its ease of integration into a line of several units.

In a preferred embodiment, the means of transfer include a carriage capable of being attached to a cassette via a retractable finger, and means of transfer capable of moving the carriage between defined positions on the path.

According to another characteristic of the invention, the tubes are placed vertically in the cassette and in line with the direction of travel, whilst the means of agitation are arranged to withdraw at least one tube laterally from the cassette and to replace it laterally into the cassette after agitation.

Advantageously, the cassette incorporates flexible U-clips allowing the removal and replacement of a tube by a lateral movement parallel to itself or by an axial movement of the tube along the axis of the latter.

The resultant advantage is that the tubes can be loaded or unloaded either via the side of the cassette or via the top of the cassette.

According to another characteristic of the invention, the pick-up mechanism or each such mechanism is capable of being driven in continuous rotation by a motor, thereby effecting continuous agitation by turning the tube through a complete revolution.

In a preferred embodiment, the means of agitation incorporate a mobile head carrying the pick-up mechanism(s) and which is capable of being driven in translational or rotational motion by means of a coupling arrangement connected to a motor with two directions of rotation.

Advantageously, this coupling arrangement includes a screw and nut and is capable of being driven in rotation by the motor in a selective manner, operating the screw either to move the mobile head away from the cassette or to bring the mobile head closer to the cassette, the mobile head in this case being prevented from rotating and fixed in a selected orientation by locking means set in a locking position.

Provision is made advantageously for these locking means to be additionally set in a release position when the coupling arrangement has arrived at a stop position at the end of the screw-in motion, thereby enabling a rotational movement of the mobile head to agitate the tube or tubes.

Preferably, the rotational movement of the mobile head is a continuous and complete rotation in the direction of the screw-in action of the coupling arrangement.

According to another characteristic of the invention, the device includes an arrangement for opening and closing the pick-up mechanism which is capable of being actuated in a translational motion by the coupling arrangement once the latter has arrived at a stop position at the end of the screw-out motion, with the mobile head being prevented from rotating by the locking means.

Advantageously, the pick-up mechanism includes two clamp elements, each of which has at least one jaw and defines a cam groove, together with a resilient return device connecting the two clamp elements to bring the jaws towards each other, the opening and closing mechanism incorporating cam fingers moved by the coupling arrangement and cooperating respectively with the cam grooves.

According to another characteristic of the invention, the device includes a means of manual loading, also referred to as the emergency loading station, placed in proximity to the transfer means and designed to hold at least one tube and to place this tube in the path of the transfer means and sampling means, when no cassette is present, to enable the collection of a sample by the sampling means.

This means of manual loading advantageously includes a rotating and tilting head having indexed positions and incorporating slots designed to accommodate tubes of different sizes.

According to a further characteristic of the invention, the sampling means include a carriage supporting a piercing device and sampling needle, and this carriage is movable between a sampling position, at which the piercing device pierces the tube bung and the sampling needle draws off a total specimen quantity, and at least one distribution position at which the sampling needle expels the said total specimen quantity, or part thereof, into a receptacle such as a reagent vessel.

Advantageously, the device additionally includes a cassette loading station and a cassette unloading station placed respectively upstream and downstream of the transfer means.

DESCRIPTION OF THE DRAWINGS

In the following description, given purely by way of example, reference is made to the attached diagrams in which:

FIGS. 6A, 7A and 8A are side views of the agitation means in different operating phases;

FIGS. 6B, 7B and 8B are top views corresponding respectively to FIGS. 6A, 7A and 8A;

DETAILED DESCRIPTION OF THE INVENTION

Figure 1:
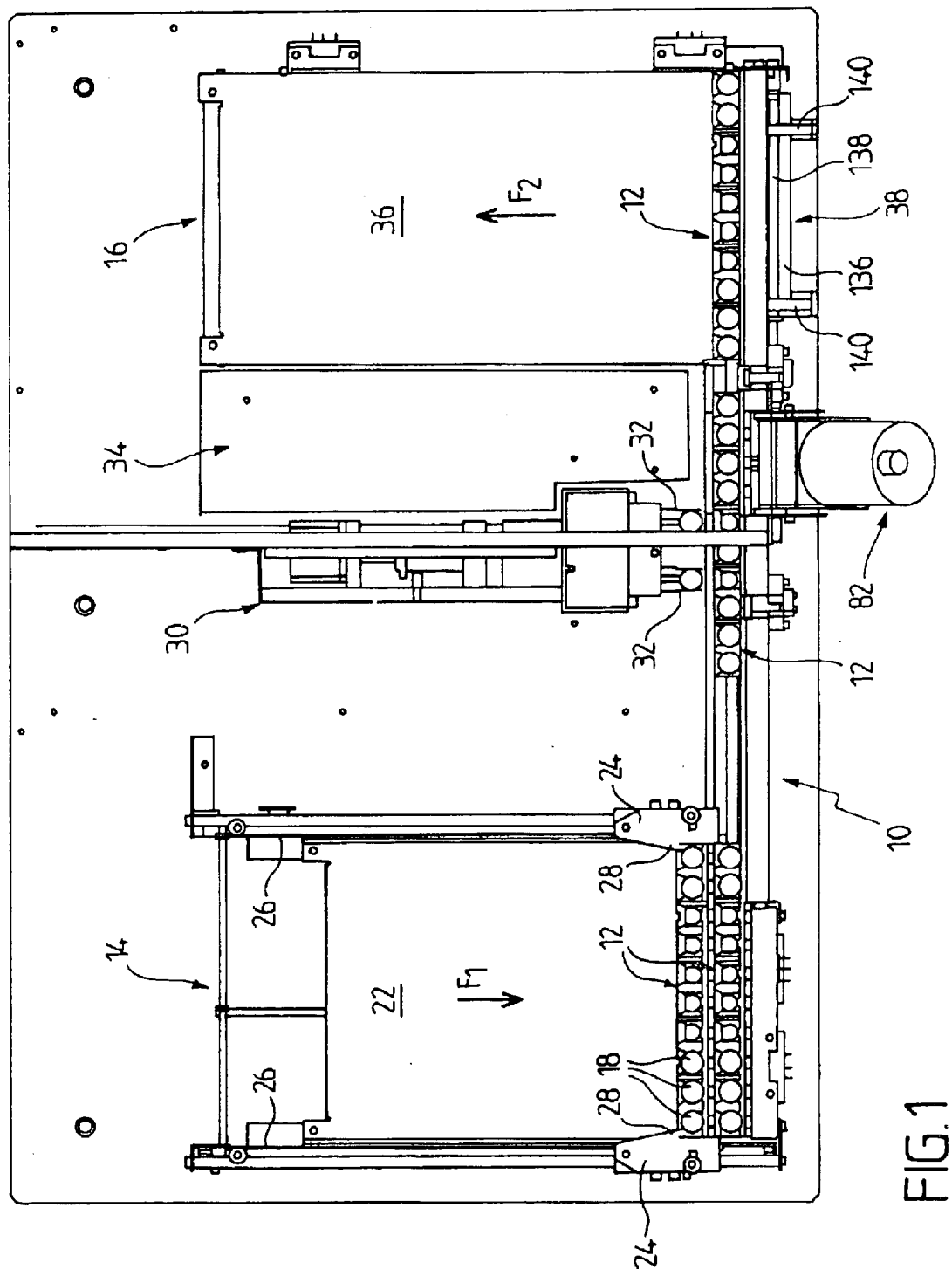
FIG. 1 is a top view of a processing device according to the invention.

The device as illustrated in its entirety in FIG. 1 includes transfer means 10 enabling cassettes 12 to be moved individually along a predetermined path, in this case a rectilinear path, between a loading station 14 and an unloading station 16. These stations 14 and 16 are placed respectively upstream and downstream of the transfer means 10.

The cassettes 12, which will be described in detail below, each carry a number of tubes 18, in this example ten tubes, each containing a blood product and each closed by means of a bung 20 (FIG. 2).

The loading station 14 includes a loading platen 22 arranged horizontally and designed to accommodate a series of cassettes holding tubes containing products to be analysed. The loading station 14 includes a forward propulsion arrangement consisting in this case of two pusher dogs 24 capable of moving synchronously in the direction of the arrow F1 to move the cassettes one by one to the transfer means 10. These pusher dogs 24 are moved in synchronism by endless belts 26 driven simultaneously, and they each incorporate a finger 28 which cooperates with one end of the cassette. These pusher dogs thus act on the last cassette forming part of the batch to be analysed.

Between the loading station 14 and the unloading station 16 are placed means of agitation, the whole of this assembly being designated by reference 30. These agitation means include, in this example, two pick-up mechanisms 32 capable of picking up two selected tubes from a cassette 12 immobilised on the path of the transfer means.

As can be seen in FIG. 1, a cassette 12 is locked in position on the path between the loading station 14 and the unloading station 16. In this example the agitation means 30, which will be described in detail below, allow two tubes to be picked up from the cassette, moved away from the cassette, agitated, then replaced in the cassette.

Between the agitation means 30 and the unloading station 16 are placed sampling means 34 which are illustrated in outline in FIG. 1 and which will be described in detail below.

These sampling means are designed to draw a sample of blood product from a tube which has been pre-agitated and replaced in the cassette. This sample is then analysed by means which will be described below.

Once all the tubes in the cassette have been agitated and a sample has been taken from each one, the entire cassette is moved by the transfer means 10 to the unloading station 16.

The latter comprises an unloading platen 36 extending horizontally and is designed to accommodate the cassettes 12 which have been moved from the transfer means 10 by ejection means 38, which will be described in detail below.

Figure 2A:
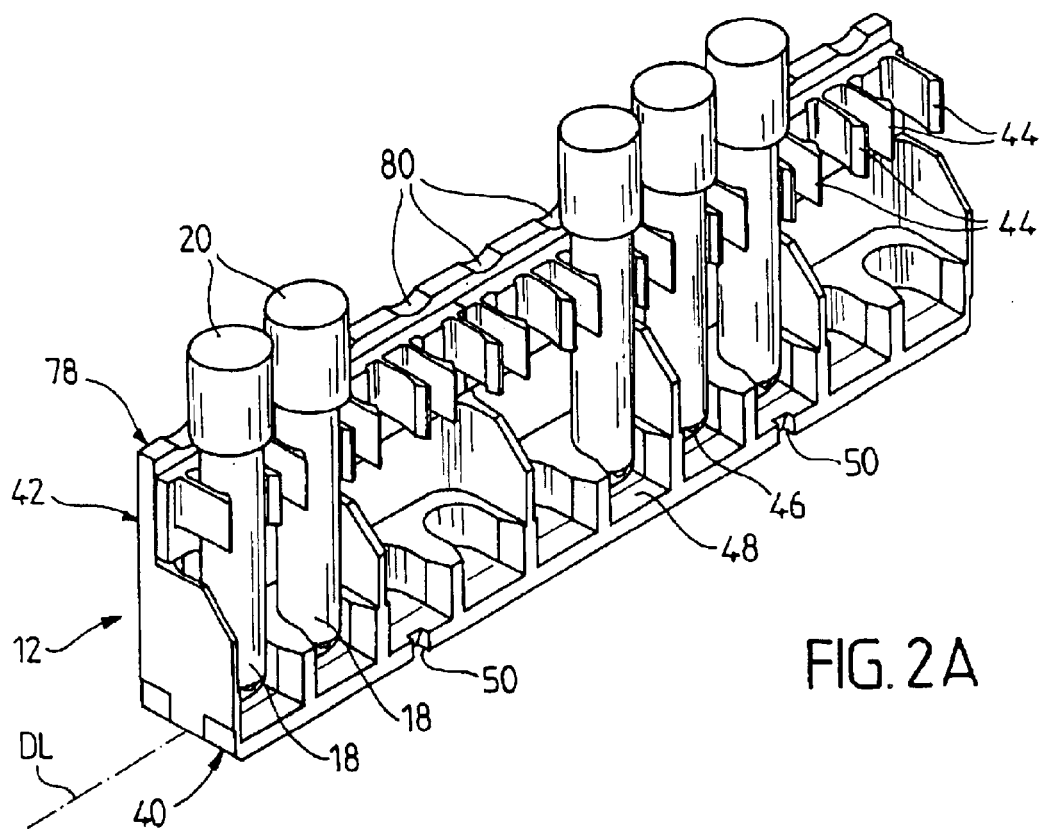
FIGS. 2A and 2B are perspective views of a cassette suitable for use in the device in FIG. 1.
Figure 2B:
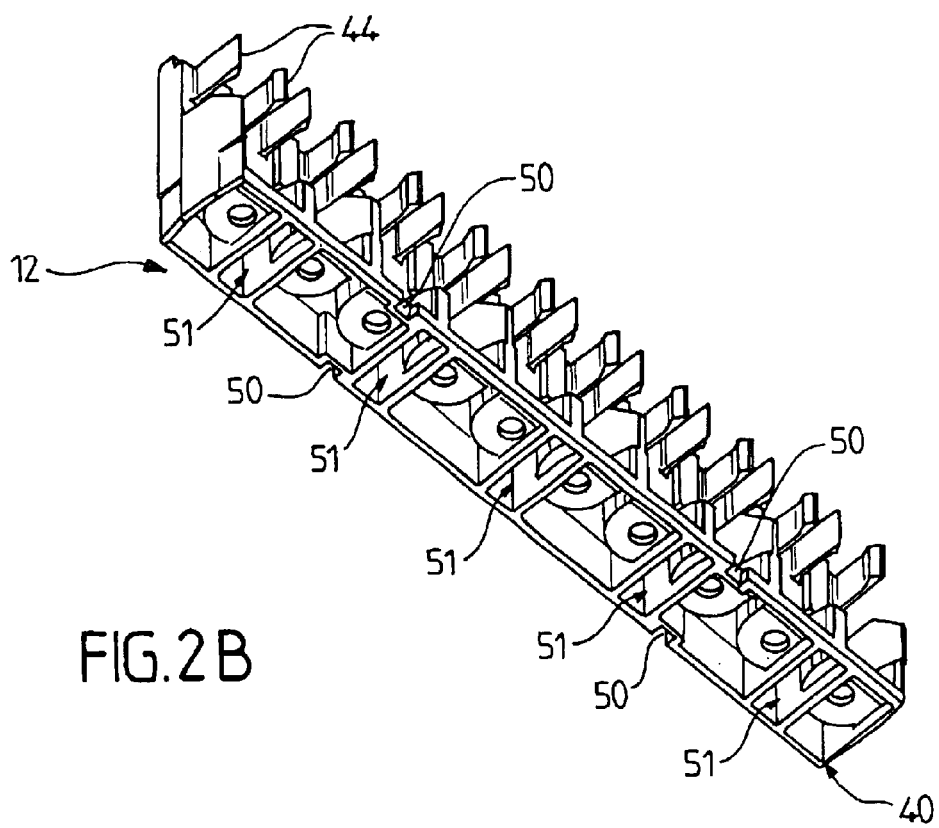

Reference will now be made to FIGS. 2A and 2B in order to describe in detail a cassette 12 in a preferred embodiment of the invention.

This cassette 12, in the form of a tube-rack, includes a base 40 generally rectangular in shape, to which is attached a vertical sidewall 42 also rectangular in shape extending over the same length as the base 40.

On its inner side, the sidewall 42 is fitted with a number of U-shaped flexible clips 44 designed to individually hold a tube 18 in a vertical position. Ten tubes can be thus disposed (in this example) in line with the longitudinal direction DL of the cassette. The tubes 18 each comprise an end 46 which fits into a slot formed in the base 40 of the cassette.

The tubes have an opening which, in this example, is directed upward and closed by means of a bung 20 which is capable of being penetrated by a piercer (not shown) forming part of the sampling means 34.

As can be seen in FIG. 2A, this cassette has the particular feature of allowing loading and unloading of the tubes via the side, i.e. in a horizontal direction and perpendicular to the sidewall 42. In other words, the removal and replacement of a tube can be effected by a sideways movement, with the tube remaining parallel to itself.

Equally, the clips 44 allow axial movement of the tube on the tube axis, i.e. a vertical movement perpendicular to the base 40.

According to the invention, it is possible to produce different types of cassettes to suit the dimensions of the tubes to be accommodated, the essential factor being that the pitch defined between the tubes remains the same.

The base 40 of the cassette incorporates four notches 50 (FIGS. 2A and 2B) designed to locate on two retractable stops (not shown) in the loading platen 22, so that the user cannot manually push the cassette into the transfer means.

In addition, five recesses 51 are provided under the cassette (FIG. 2B) to cooperate with the transfer means, as will be seen below, thereby causing the cassette to be moved on a pre-determined path.

Figure 3:
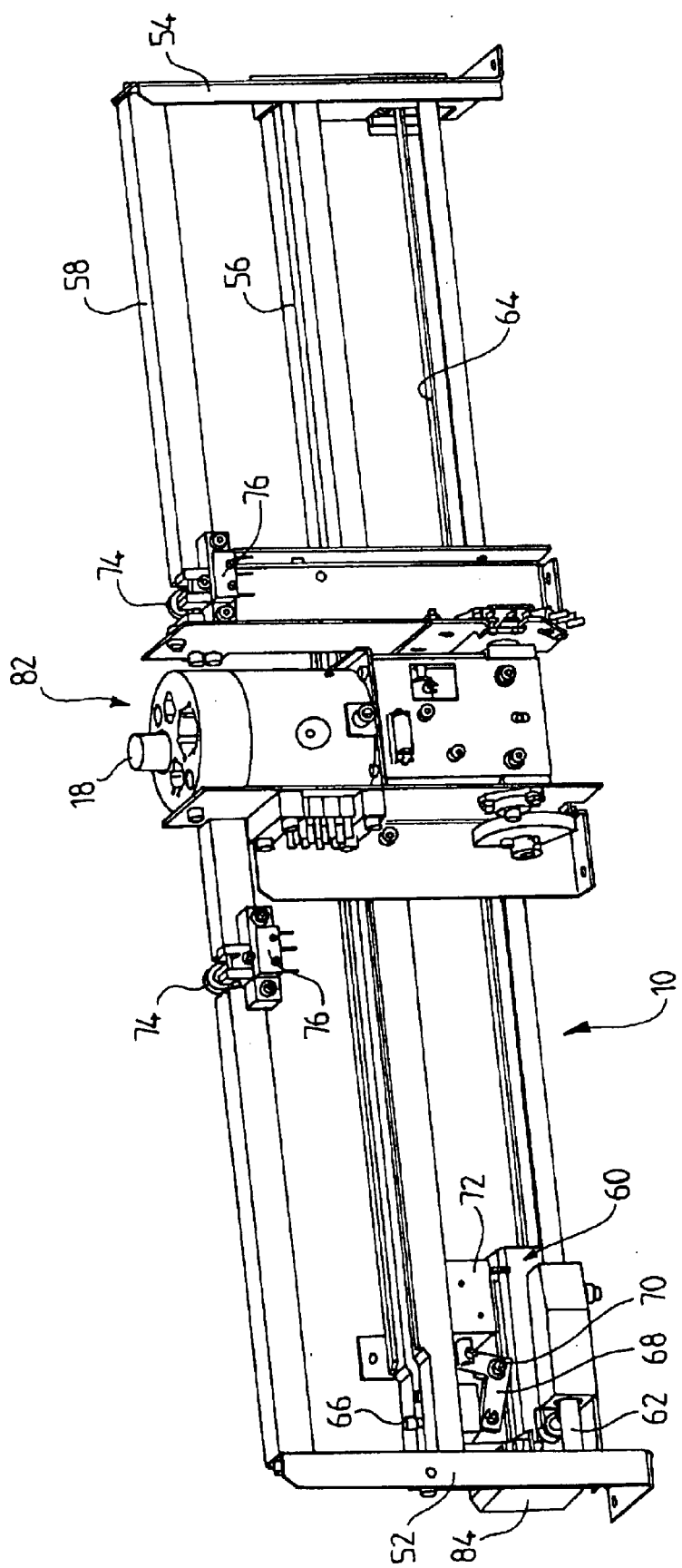
FIG. 3 is a perspective view of the transfer means and manual loading station.

The transfer means 10, as illustrated in FIG. 3, include two end brackets 52 and 54 between which extend a horizontal guide rail 56 along which slides the base 40 of a cassette, and a further horizontal guide rail 58, placed above the guide rail 56 and against which the sidewall 42 of the cassette bears laterally. The rails 56 and 58 are each made up of two sections. The cassette can thus be guided as it travels with its base 40 and its sidewall 42 bearing respectively on the rails 56 and 58.

The translational motion of a cassette is effected by means of a carriage 60 arranged to travel along a rectilinear guide element 62, such as a rod, extending parallel to the rail 56. The transfer means 10 include an endless belt 64 coupled to the carriage 60 and which is designed to move the carriage, in either direction, between defined positions on the travel path.

The carriage 60 is fitted with a retractable finger 66 connected to an L-shaped lever 68 arranged to pivot about a pin 70 and actuated by an electromagnet 72. This retractable finger is capable of being moved upward to engage in one or other of the recesses under the cassette. It can also be moved vertically downward to retract from the cassette and allow, in particular, ejection of the latter onto the unloading platen 36.

Also, the guide rail 58 is fitted with two mobile stops 74, at least one of which is capable of being actuated as the cassette travels in the transfer means 10.

To this end, the side wall 42 of the cassette includes an indented edge 78 incorporating a series of notches 80 spaced at the same pitch as the tubes.

Each of the mobile stops 74 is also capable of actuating a sensor 76. When at rest, each mobile stop 74 is held in the lower position by means of a spring and the sensor 76 is at rest.

During lateral movement of the cassette, the stop 74 is caused to rise vertically upward by the indented edge 78 of the wall 42 of the cassette 12, the effect of which is to actuate the sensor 76. The stop 74 reverts to its initial position when it drops into a slot 80, and the sensor is no longer activated.

The combination of information received from the sensors 76 actuated by the stops provides a means of determining the position of at least one cassette in the transfer means 10 and is also used to maintain the position of the cassette during the operations of sampling, agitation and manipulation of a second cassette by the carriage 60.

As can be seen in FIGS. 1 and 3, beside the transfer means 10 is placed a means of manual loading 82, also referred to as an emergency loading station, which is designed to accommodate at least one tube 18 and to place it in the path of the transfer means and sampling means, when no cassette is present, for the purposes of collecting a sample using the sampling means 34. This method of loading will be described in detail below.

The translational motion of the endless belt 64 is driven in one direction or the other by a motor 84, in particular of the stepper type, enabling the carriage and therefore the cassette to be placed in a selected position along the travel path.

Figure 4:
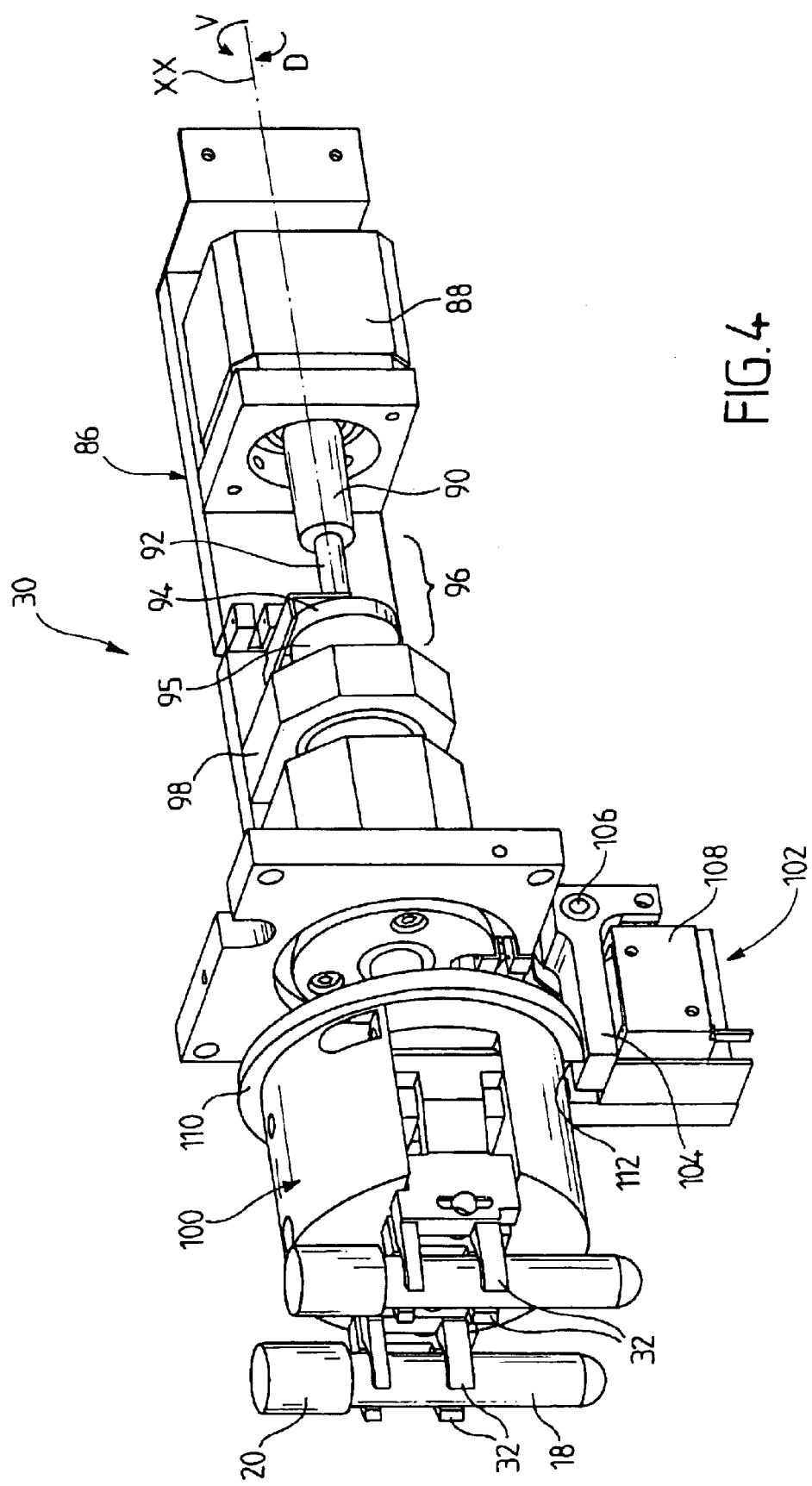
FIG. 4 is a perspective view of the agitation means.
Figure 5:
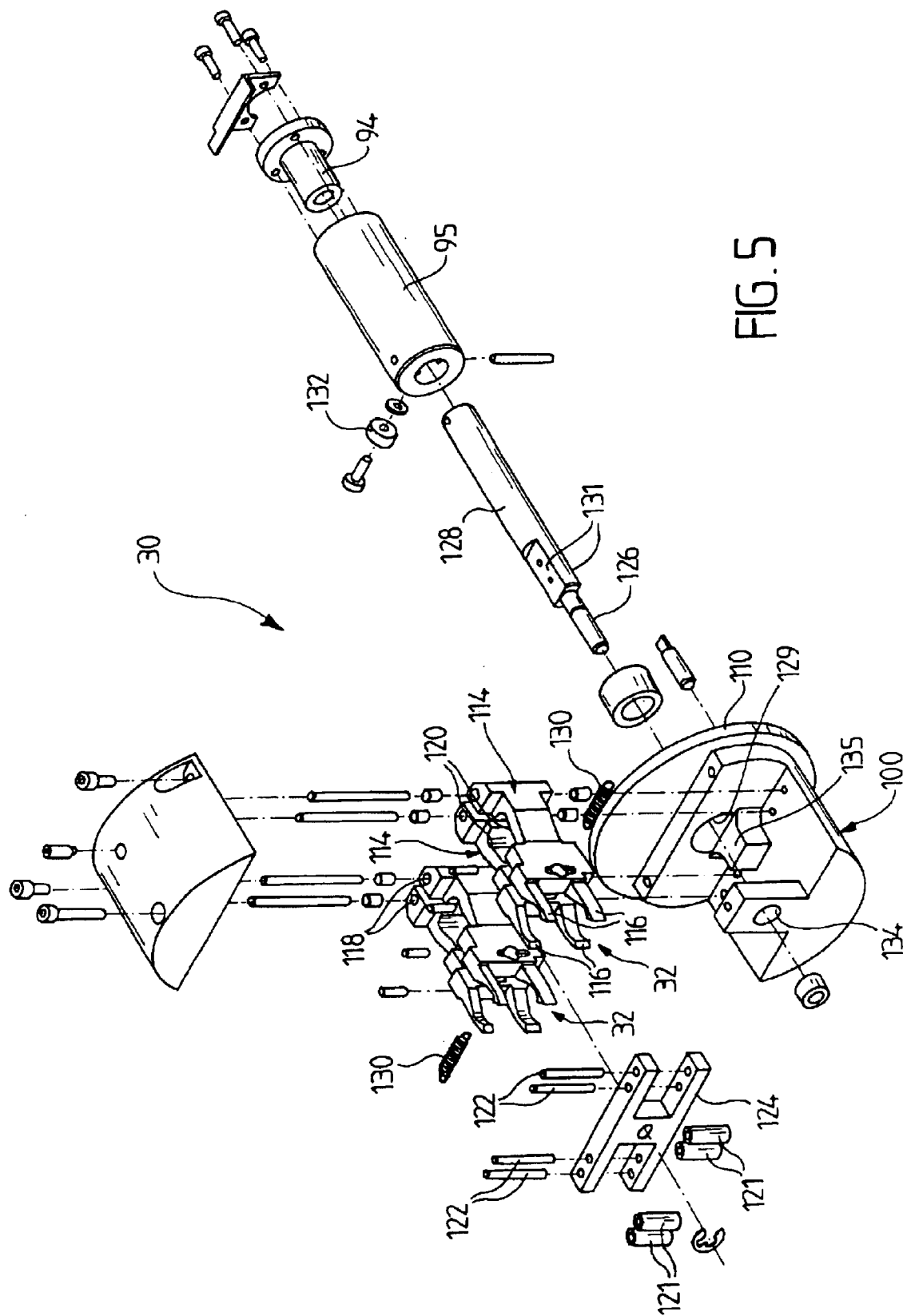
FIG. 5 is an exploded perspective view of the agitation means in FIG. 4.

Reference will now be made to FIGS. 4 and 5 together to describe the means of agitation 30. The latter comprise a bracket 86 supporting an electric motor 88, of the stepper type, incorporating a shaft 90 extending in a horizontal axial direction X—X which is perpendicular to the direction of travel of the cassettes on the transfer means 10, i.e. perpendicular to the path described by the travel means 10.

The shaft 90 carries a screw 92 (threaded rod) operating in conjunction with a nut 94 to form a mechanism 96 of the screw/nut type (FIGS. 4 and 5). The nut 94 is fixed to a sleeve 95 guided in a flange 98 and is connected to a mobile head 100 which supports the two pick-up elements 32.

The electric motor 88 can be operated to rotate in either direction, under defined conditions, to selectively obtain either linear movement of the mobile head 100 in the direction of the axis X—X, or rotational movement of the head about this axis.

The agitation means 30 also include a stop assembly 102 composed of a lever 104 arranged to pivot about a pin 106 and actuated be means of an electro-magnet 108. The lever 104 is arranged to cooperate with a disk 110 integral with the mobile head 100 and incorporating a notch 112. This stop assembly can be set selectively either in a locking position in which the mobile head 100 is prevented from moving axially, or in a release position in which the mobile head is free to move axially and in rotation with the nut.

The motor 88 can be driven in rotation in a direction V corresponding to a screw-in action, which causes the nut 94 (and therefore the mobile head 100) to move towards the motor 88, the mobile head being prevented from rotating by locking means. The latter are composed of a bearing 132 and a groove 133 and will be described in detail below with reference to FIG. 6. This movement thus makes it possible to move the mobile head away from a cassette placed on the transfer means.

The motor 88 can also be driven in a direction D corresponding to an unscrewing action which causes the nut 94 (and therefore the mobile head 100) to move away from the motor 88, with the mobile head again being prevented from rotating by the locking means 132 and 133.

This movement has the opposite effect of moving the mobile head 100 towards the cassette placed on the transfer means.

In addition, when the motor 88 is actuated in the screw-in direction and the nut 94 is brought up against the shaft 90 of the motor 88, and the locking means 132 and 133 are placed in the unlocked position, rotation of the motor in the screw-in direction allows the mobile head 100 to be rotated, when the latter is retracted away from the cassette, as will be seen below.

As can be seen more particularly in FIG. 5, each of the pick-up mechanisms 32 comprises two clamping assemblies 114 each having two jaws 116 and is arrange to pivot about a pin 118. Each clamping assembly defines a cam groove 120 of a chosen configuration which is designed to work in conjunction with a cam finger 121. The device here includes four cam fingers 121 carried by the pins 122 on an H-bracket 124 mounted at the end 126 of a rod 128, itself mounted at the end of the sleeve 95.

Also, the two jaws of the same clamp are drawn together by the action of a resilient return spring 130 allowing the jaws to adapt to the different diameters of the tubes used. The rod 128 is capable of sliding axially and with a linear movement into an aperture 129 in the disk 110, whilst its end 126 is capable of sliding into an aperture 134 in the mobile head. The rod 128 incorporates two flats 131 one of which bears against a base 135 on the mobile head 100, enabling the rod 128 and the head 100 to be locked and rotated or released according to their mutual axial position.

Thus, when the rod 128 is caused to moved axially relative to the mobile head 100, it opens and closes the respective jaws 116 of the two pick-up mechanisms.

Figure 6A:
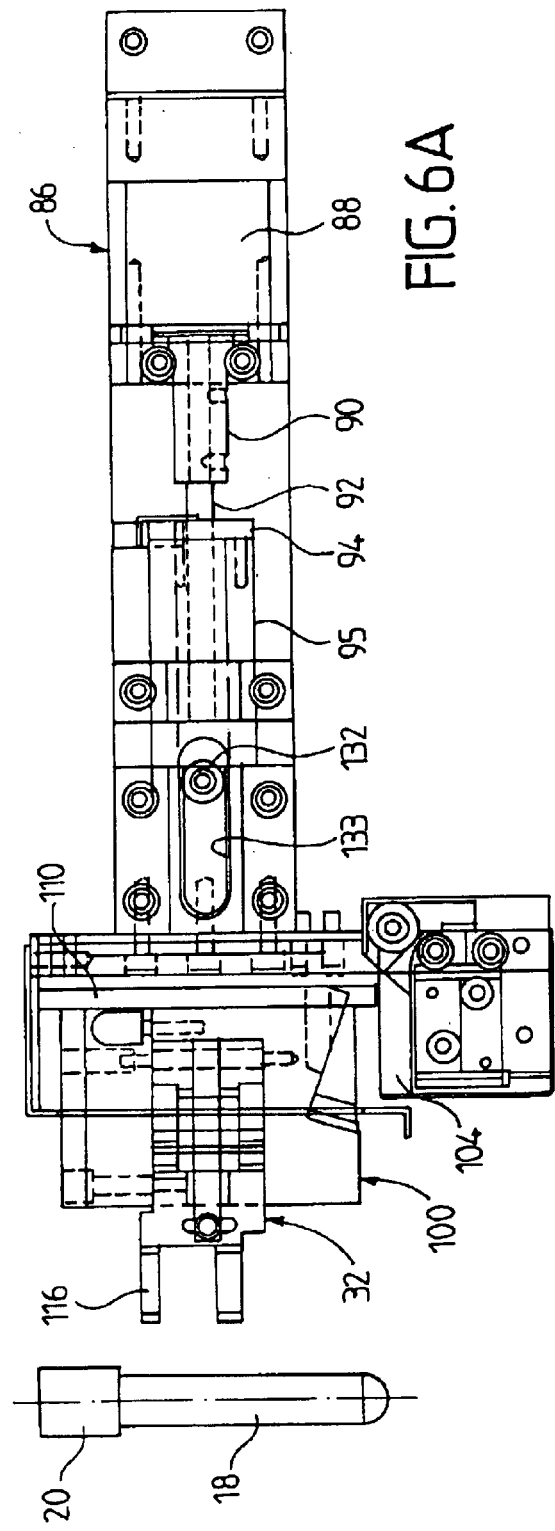
Figure 6B:
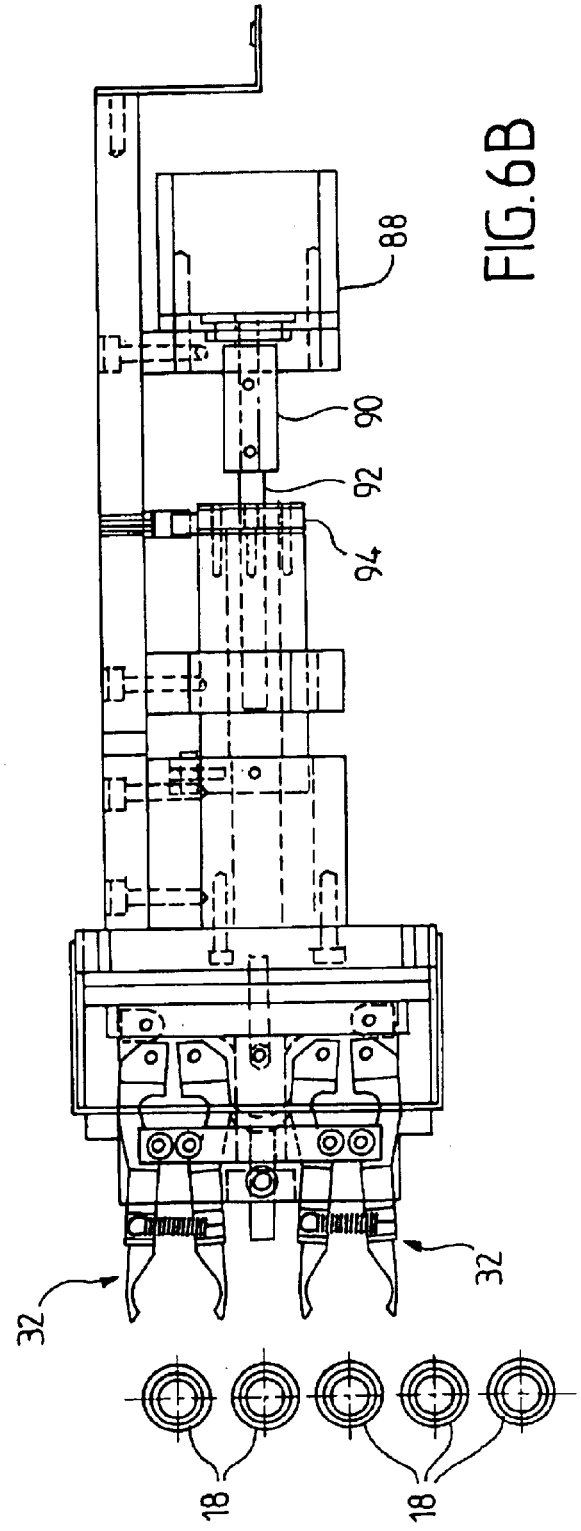

Operation of the agitation means will now be described with reference to FIGS. 6 to 8. In the position shown in FIGS. 6A and 6B, the mobile head 100 is in a position retracted from the cassette and therefore from the tubes held in the latter. The coupling arrangement is close to a stop position at the end of the screw travel. The aforementioned locking means are composed of a bearing 132 integral with a sleeve 95 and which operates in conjunction with the groove 133 of the bracket. These means are used to lock off the travel motion only or the rotational movement only.

If the motor 88 is actuated in the screw-out direction, the mobile head 100 moves towards the cassette and therefore towards the tubes held in the latter. The head comes into contact with a front plate (not shown) which will come into play later when the tube is replaced in the cassette. The head thus assumes the position illustrated in FIGS. 7A and 7B, in which the jaws 116 of the pick-up mechanisms are open ready to each pick up a tube from the cassette. The stop assembly 102 is then actuated to set the lever 104 in the locking position shown dotted (reference 104'). This has the effect of locking the head in the axial direction. The motor 88 is then operated in the screw-in direction, which first causes the pick-up elements to pivot bringing their respective jaws together to each pick up a tube from the cassette.

The locking means are then returned to the release position, as illustrated in FIGS. 8A and 8B, and operation of the motor 88 in the screw-in direction is continued to move the mobile head away from the cassette, with the pick-up mechanism each holding a tube. During this movement, the mobile head is prevented from rotating by the fact that the bearing 132 remains engaged in the groove 133.

When the end of the screw-in motion is reached, i.e. at the stop position between the nut 94 and the shaft 90, the bearing 132 moves out of the groove 133, so that rotation of the mobile head is no longer locked.

The motor can then be actuated, in a continuous manner, in the screw-in direction which causes the mobile head to rotate, thereby agitating the two tubes which it is holding.

These two tubes are then agitated by a continuous rotational movement through 360°, which provides a better agitation action than a pendulum motion.

After agitation, the tubes are replaced in the cassette.

Thus, by virtue of the motor 88, the coupling arrangement 96, the stop assembly 102 and the locking means comprising the bearing 132 and the groove 133, various movements can be obtained, namely a translational movement of the mobile head 100 in the axial direction, in one direction or the other, and a rotational movement of said mobile head to provide agitation of the tubes.

It will be noted that, in the embodiment described, the means of agitation remove two tubes from the cassette each time, which are agitated and then replaced in the cassette.

As this cassette holds a total of ten tubes, a minimum of five operations is needed to complete the agitation of all ten tubes. It is preferred however to agitate each tube twice: first tube 1 by itself, then tube 2 by itself, then tubes 1 and 3 together, then tubes 2 and 4 together, and so on.

Each time, the cassette is moved forward on the transfer means by a chosen distance defined by the stepper motor 84 which drives the motion of the carriage 60.

The pre-agitated tubes are then positioned one by one at the sampling means 32, which will be described below.

After taking samples from all ten tubes in the cassette, the latter is taken to the unloading station 16 where the carriage mechanically actuates the ejection means 38. The latter comprise a tilting assembly 136 (FIG. 1) arranged to pivot about a pin extending parallel to the direction of the transfer means and which incorporates a ramp 138 against which the carriage 60 bears to initiate the pivoting motion of the tilting assembly. The latter is fitted with two pushers 140 which bear against the cassette to move it onto the platen 36 in the direction of the arrow F2. Thus, following the analysis, the batch of cassettes is accommodated on the platen 36 of the unloading means.

Figure 9:
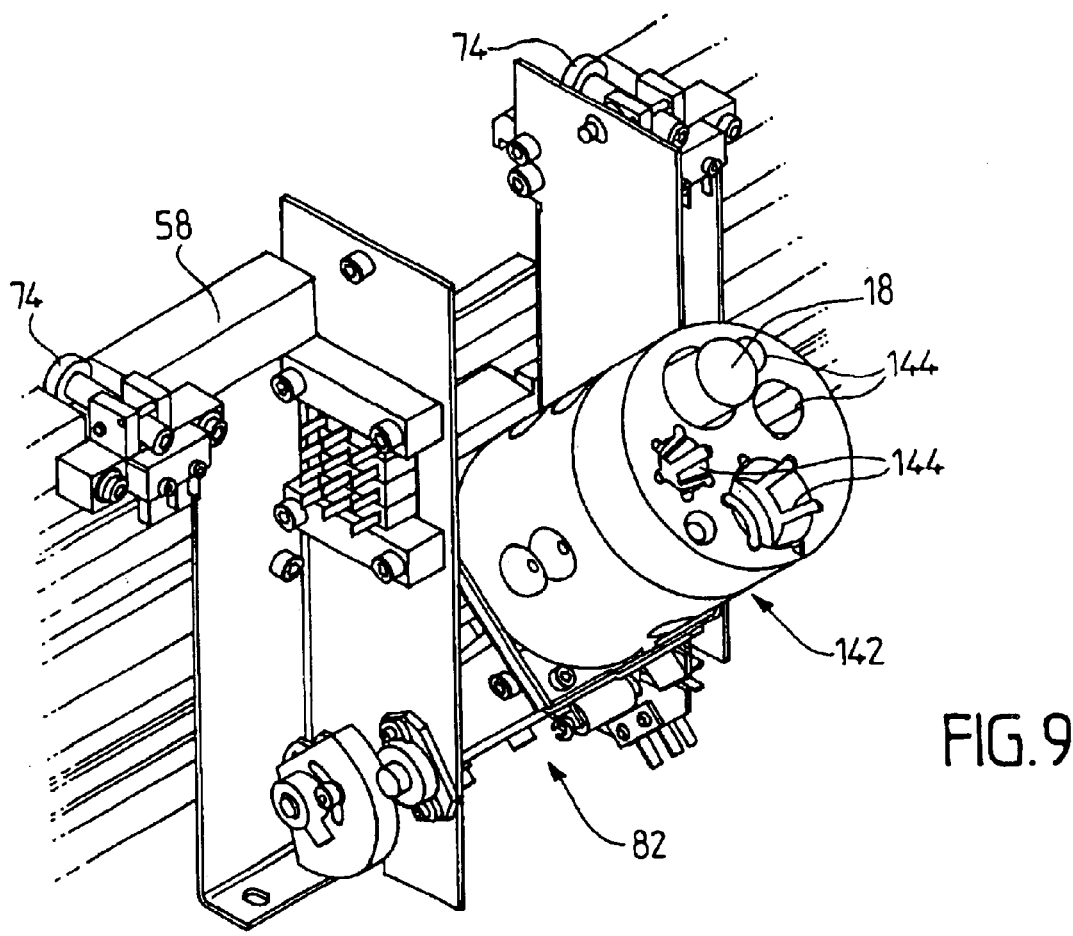
FIG. 9 is a partial perspective view of the transfer mechanism showing the manual loading station in an inclined position for loading.
Figure 10:
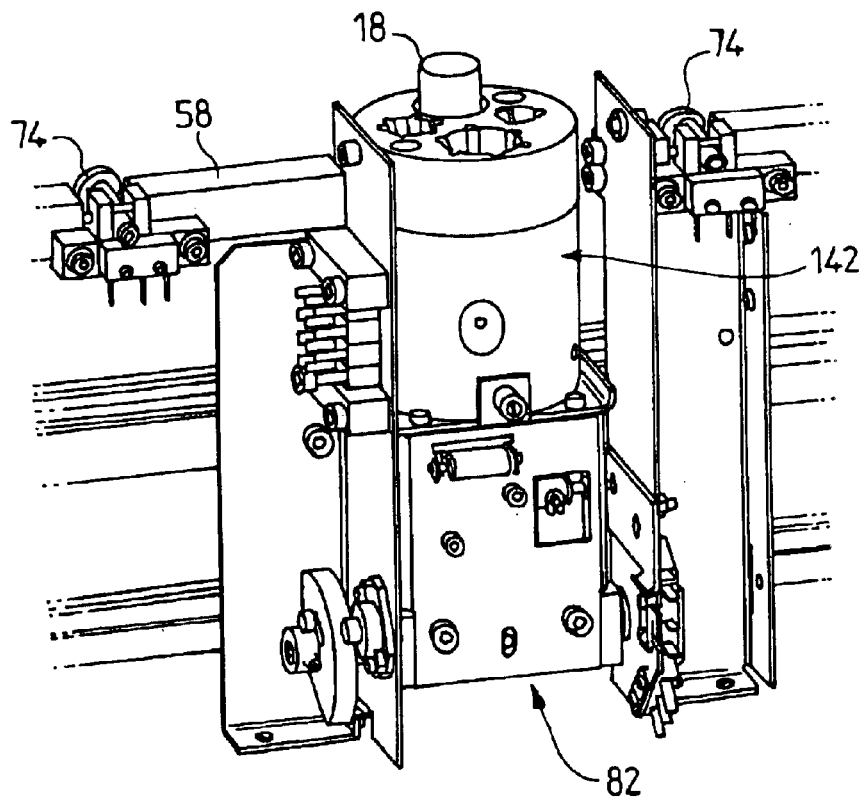
FIG. 10 is a view similar to FIG. 9 in which the loading station is in the upright position.

Reference will now be made to FIGS. 9 and 10 to describe in greater detail the manual loading means 82, also referred to as the emergency loading station.

The latter is placed in proximity to the transfer means 10 and is capable of accommodating at least one tube 18, without the presence of a cassette on the transfer means. It includes a head 142 arranged to rotate and tilt and capable of being placed in various indexed positions. This head incorporates slots 144 adapted to accommodate tubes of different sizes.

The head 142 can be placed in an inclined position, as shown in FIG. 9, enabling at least one tube to be loaded into an appropriate slot. This head is then tilted back to a vertical position, as shown in FIG. 10, in which the tube 18 is vertical thereby facilitating the collection of a sample of blood product. As can be seen in FIGS. 9 and 10, the head can be rotated into different indexed positions in which the slot holding the tube to be analysed is positioned opposite the sampling means 34.

Figure 11:
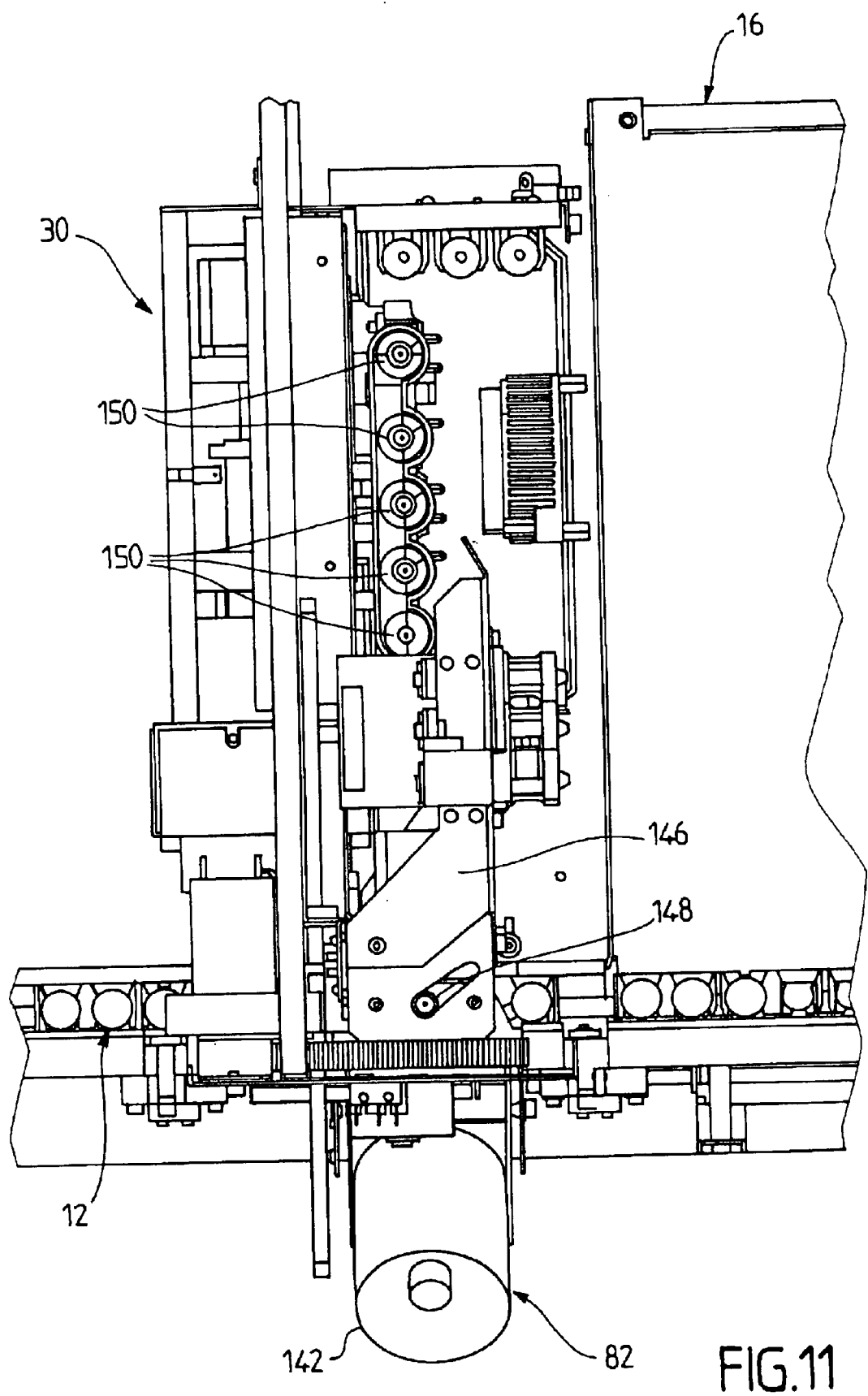
FIG. 11 is a top view of the sampling means.

Reference will now be made to FIG. 11 to describe the general structure of the sampling means. The latter comprise a carriage 146 which can be made to travel horizontally in a direction orthogonal to that of the transfer means.

This carriage 146 supports a piercer and an associated sampling needle (designated together by reference 148) and can be positioned above the tube of which the bung is to be pierced. The piercer and the needle are then moved vertically up and down to pierce the tube bung and draw off a total sample quantity. For this purpose, the sampling needle is connected to a suitable suction pump (not shown). The needle and piercer are then raised and the carriage is moved away to distribute portions of the sample collected into various vessels 150 where a portion of the sample is mixed each time with a suitable reagent for analysis purposes.

By way of example, the sampling means may be realised in accordance with the indications given in document EP-A-0 634 660. In particular, these sampling means advantageously incorporate means of cleaning to clean the needle before and after each sampling operation.

A compact device is thus obtained that can be readily integrated into a line of haematological instruments, especially as the cassettes are moved in a linear manner by the transfer means between a loading station and an unloading station.

By virtue of the fact that the tubes are agitated independently of the cassettes, the means of agitation provided for this purpose occupy less space and can be more readily integrated into the arrangements of the invention.

The device disclosed also has the advantage that the tubes can be loaded or unloaded into/from the cassettes either sideways or vertically, in particular from above.

Furthermore, by virtue of the fact that sampling takes place from tubes that have been pre-agitated and replaced in the cassette, it is not necessary to provide means to hold the tubes in position for sampling.

Of course, the invention is not limited to the embodiment described above by way of example, and can be extended to other variants.

The invention is particularly applicable to haematological analysers such as those used in laboratories for analysis purposes.

What is claimed is:

1. The device for processing samples of blood products contained in tubes which are closed by means of bungs and loaded into cassettes, said device comprising: means of agitation for agitating the tubes, and means for sampling and collecting at least one sample from a pre-agitated tube, the improvement comprising: transfer means (10) for moving the cassettes (12) individually on a pre-determined path, means for immobilising the cassettes on said path and wherein the means of agitation (30) incorporates at least one pick-up mechanism (32) capable of picking up at least one selected tube (18) from one of the cassettes (12) immobilised on the path, removing said at least one selected tube away from the one cassette, agitating said at least one selected tube and replacing said at least one selected in the one cassette, and wherein the means for sampling (34) includes at least one needle (148) capable of drawing a given sample quantity from the at least one selected tube that has been pre-agitated and replaced in the cassette, wherein the pick-up mechanism (32) or each such mechanism is capable of being driven in continuous rotation by a motor (88), thereby effecting continuous agitation by turning the tube through a complete revolution.

2. The device according to claim 1, wherein the means of transfer (10) include a carriage (60) capable of being attached to a cassette (12) via a retractable finger (66), and means of transfer (64, 68) capable of moving the carriage between defined positions on the path.

3. The device according to claim 1, in which the tubes (18) are placed vertically in the cassette (12) and in line with the direction of travel, and in that the means of agitation (30) are arranged to withdraw at least one tube (18) laterally from the cassette and to replace it laterally into the cassette after agitation.

4. The device according to claim 1, in which the cassette (12) incorporates flexible U-clips (44) allowing the removal and replacement of a tube by a lateral movement parallel to itself or by an axial movement of the tube along the axis of the latter.

5. The device according to claim 1, in which the means of agitation (30) incorporate a mobile head (100) carrying the pick-up mechanism(s) (32) and which is capable of being driven in linear or rotational motion by means of a coupling arrangement (96) connected to a motor (88) with two directions of rotation.

6. The device according to claim 5, in which the coupling arrangement (96) includes a screw (92) and nut (94) and is capable of being driven in rotation by the motor (88) in a selective manner, operating the screw either to move the mobile head (100) away from the cassette (12) or to bring the mobile head (100) closer to the cassette (12), the mobile head being prevented from rotating and fixed in a selected orientation by locking means (132, 133) set in a locking position.

7. The device according to claim 6, in which the locking means (132, 133) are capable of being set in a release position when the coupling arrangement (96) has arrived at a stop position at the end of the screw-in motion, thereby enabling a rotational movement of the mobile head (100) to agitate the tube(s).

8. The device according to claim 5, in which the rotational movement of the mobile head (100) is a continuous and complete rotation in the direction of the screw-in action of the coupling arrangement (96).

9. The device according to claim 5, which includes an arrangement for opening and closing the pick-up mechanism (32) which is capable of being actuated in a translational motion by the coupling arrangement (96) once the latter has arrived at a stop position at the end of the screw-out motion, with the mobile head (100) being prevented from rotating by the locking means (132, 133).

10. The device according to claim 9, in which the pick-up mechanism (32) includes two clamp elements (114), each of which has at least one jaw (116) and defines a cam groove (120), together with a resilient return device (130) connecting the two clamp elements to bring the jaws towards each other, and in that the opening and closing mechanism incorporates cam fingers (122) moved by the coupling arrangement (96) and cooperating respectively with the cam grooves (120).

11. The device according to claim 1, which includes a means of manual loading (82) placed in proximity to the transfer means (10) and designed to hold at least one tube (18) and to place this tube in the path of the transfer means and sampling means, when no cassette is present, to enable the collection of a sample by the sampling means (34).

12. The device according to claim 11, in which the means of manual loading (82) includes a rotating and tilting head (142) having indexed positions and incorporating slots (144) designed to accommodate tubes of different sizes.

13. The device according to claim 1, in which the sampling means (34) include a carriage (146) supporting the piercing device and sampling needle (148), and in that the carriage is movable between a sampling position, at which the piercing devise pierces the tube bung and the sampling needle draws off a total specimen quantity, and at least one distribution position at which the sampling needle expels the said total specimen quantity, or part thereof, into a receptacle such as a reagent vessel.

14. The device according to claim 1, which includes a cassette loading station (14) and a cassette unloading station (16) placed respectively upstream and downstream of the transfer means (10).

* * * * *